United States Patent
Gorka et al.

(10) Patent No.: US 10,202,632 B2
(45) Date of Patent: *Feb. 12, 2019

(54) ENZYMATIC DETERMINATION OF HBA1C

(71) Applicant: DiaSys Diagnostic Systems GmbH, Holzheim (DE)

(72) Inventors: Günther Gorka, Bad Camberg (DE); Yoshifumi Watazu, Kobe (JP); Erwin Metzmann, Marburg (DE); Alexandra Lein, Diez (DE); Holger Müller, Diez (DE); Matthias Grimmler, Elz (DE)

(73) Assignee: DiaSys Diagnostic Systems GmbH, Holzheim (DE)

( * ) Notice: Subject to any disclaimer, the term of this patent is extended or adjusted under 35 U.S.C. 154(b) by 141 days.

This patent is subject to a terminal disclaimer.

(21) Appl. No.: 15/308,640

(22) PCT Filed: Mar. 31, 2015

(86) PCT No.: PCT/EP2015/057024
§ 371 (c)(1),
(2) Date: Nov. 3, 2016

(87) PCT Pub. No.: WO2015/169511
PCT Pub. Date: Nov. 12, 2015

(65) Prior Publication Data
US 2017/0191112 A1 Jul. 6, 2017

(30) Foreign Application Priority Data

May 6, 2014 (DE) .................. 10 2014 106 301

(51) Int. Cl.
| | |
|---|---|
| *C12Q 1/28* | (2006.01) |
| *G01N 33/72* | (2006.01) |
| *C12Q 1/26* | (2006.01) |
| *C12Q 1/37* | (2006.01) |
| *C12N 9/64* | (2006.01) |

(52) U.S. Cl.
CPC .......... *C12Q 1/28* (2013.01); *C12N 9/6491* (2013.01); *C12Q 1/26* (2013.01); *C12Q 1/37* (2013.01); *C12Y 105/03* (2013.01); *C12Y 304/24027* (2013.01); *G01N 33/723* (2013.01); *G01N 33/725* (2013.01); *C12Q 2326/00* (2013.01); *G01N 2333/805* (2013.01); *G01N 2333/90672* (2013.01); *G01N 2333/954* (2013.01)

(58) Field of Classification Search
None
See application file for complete search history.

(56) References Cited

U.S. PATENT DOCUMENTS

| | | | |
|---|---|---|---|
| 5,541,117 A | 7/1996 | Karl et al. | |
| 5,631,140 A * | 5/1997 | Kobold | C12Q 1/37 435/23 |
| 6,562,581 B2 | 5/2003 | Law et al. | |
| 6,790,665 B2 | 9/2004 | Yonehara et al. | |
| 2007/0224685 A1 | 9/2007 | Kouzuma et al. | |
| 2008/0295259 A1 | 12/2008 | Ueda et al. | |
| 2012/0288875 A1* | 11/2012 | Grenier | G01N 33/9493 435/7.8 |
| 2013/0078664 A1 | 3/2013 | Yuan et al. | |
| 2013/0115646 A1 | 5/2013 | Soya et al. | |
| 2013/0130401 A1 | 5/2013 | Kanda et al. | |
| 2013/0164273 A1 | 6/2013 | Zimmerman et al. | |
| 2013/0266951 A1 | 10/2013 | Will | |
| 2017/0058318 A1 | 3/2017 | Gorka et al. | |

FOREIGN PATENT DOCUMENTS

| | | |
|---|---|---|
| CN | 101358229 A | 2/2009 |
| CN | 106574933 A | 4/2017 |
| EP | 0 038 205 A1 | 10/1981 |
| EP | 0 045 220 A1 | 2/1982 |
| EP | 0 124 287 A2 | 11/1984 |

(Continued)

OTHER PUBLICATIONS

First Chinese Office Action dated Jan. 26, 2018 issued in corresponding Chinese Patent Application No. 201580023396.4 (5 pages) and its English-language translation thereof (10 pages).
S. Latt et al, "Thermolysin: A Zinc Metalloenzyme", Biochemical and Biophysical Research Communications, vol. 37, No. 2, 1969, p. 333-p. 339.
I. Sakurabayashi et al., "New Enzymatic Assay for Glycohemoglobin", Clinical Chemistry, vol. 49, No. 2, 2003, p. 269-p. 274.
S. Ferri et al., "Review of Fructosyl Amino Acid Oxidase Engineering Research: A Glimpse into the Future of Hemoglobin A1c Biosensing", Journal of Diabetes Science and Technology, vol. 3, Issue 3, May 2009, p. 585-p. 592.

(Continued)

*Primary Examiner* — Susan M Hanley
(74) *Attorney, Agent, or Firm* — Drinker Biddle & Reath LLP

(57) ABSTRACT

A method for determining the amount of glycated hemoglobin (HbA1c), in which—if required—the erythrocytes in a sample are hemolyzed, the haemoglobin that is then released—if required—is contacted with a proteolytic agent and the glycated hemoglobin degradation products obtained in this way or otherwise are quantified is disclosed. In order to provide such a process and reagents employable therein that has/have the property of sufficient stability of the chemical compounds that are essential to the reaction, the provision of the requisite proteolytic agent in the form of an inactivated protease is proposed, which is then only reactivated in situ. For the stabilization of the hemoglobin, which is unfolded at a very low pH in the range from 1 to 3, at least one suitable stabilizer should be present in the hemolysis solution, and, where a leuco dye is used in connection with the determination of the amount of HbA1c, it is proposed that the latter be stabilized with particular phosphine compounds and/or thio compounds.

18 Claims, 3 Drawing Sheets

(56) References Cited

FOREIGN PATENT DOCUMENTS

| EP | 2 161 333 A1 | 3/2010 | | |
|----|----|----|----|----|
| EP | 2 357 228 A1 | 8/2011 | | |
| EP | 2 604 698 A1 | 6/2013 | | |
| EP | 2 813 854 A1 | 12/2014 | | |
| GB | 2248452 A | * | 4/1992 | ......... C11D 3/38663 |
| JP | S62-294584 A | 12/1987 | | |
| KR | 10 1994 0 005 615 B1 | 6/1994 | | |
| WO | WO-2008/013874 A1 | 1/2008 | | |
| WO | WO-2011/126067 A1 | 10/2011 | | |
| WO | WO-2013/118960 A1 | 8/2013 | | |

OTHER PUBLICATIONS

Office Action dated Feb. 20, 2018 issued in related U.S. Appl. No. 15/308,531 with double-patenting rejection on pp. 10-12.

N.P. Balaban, et al., Metalloproteazy batsill. Klassifikatsiya, strukturnyye osobennosti i termostabil'nost' belkov [Translation: Classification, structural features and thermal stability of proteins] / Yestestvennyye nauki, 2007, vol. 149, book 2, pp. 7-23.

Russian Office Action dated Nov. 6, 2018 issued in corresponding Russian Patent Application No. 2016147532 (6 pages) and its English-language translation thereof (4 pages).

* cited by examiner

ENZYMATIC DETERMINATION OF HBA1C

CROSS REFERENCE TO RELATED APPLICATIONS

This application is a National Stage of International Application No. PCT/EP2015/057024 filed Mar. 31, 2015, which claims benefit of German Patent Application No. 10 2014 106 301.5 filed May 6, 2014, both of which are herein incorporated by reference in their entirety.

TECHNICAL FIELD

The present invention concerns a method of determining the amount of glycated haemoglobin (HbA1c) in a sample and a reagent kit which can be used in a method of determining the amount of glycated haemoglobin (HbA1c) in a sample.

BACKGROUND OF THE INVENTION

In accordance with the definition of the IFCC (International Federation of Clinical Chemistry and Laboratory Medicine) glycated haemoglobin (HbA1c) is the stable product of a coupling of glucose to the N-terminal valine of the beta chain of the haemoglobin and the amount of HbA1c in relation to the amount of overall haemoglobin (mmol HbA1c per mol total haemoglobin) is representative of the average blood glucose level of the last eight weeks before the blood sample was taken and is therefore also referred to as "long-term blood sugar". The HbA1c value which should normally be in the range of 20 to 42 mmol/mol is therefore an important indicator for the diagnosis and treatment of diabetes mellitus.

Known methods of determining HbA1c are for example immunoassays, for example turbidimetric immunoassays (TIA) and high power liquid chromatography (HPLC). An enzymatic method has also been available for some time, in which a reaction of glycated haemoglobin with a fructosyl amino acid oxidoreductase (FAOD) is quantified.

In the enzymatic investigation—as moreover is also the case with all other HbA1c methods—the first step is to haemolytically rupture the erythrocytes in the blood sample to release the HbA1c contained therein. The released glycated haemoglobin is then brought into contact with a proteolytic agent to produce glycated haemoglobin degradation products. Those proteolytically produced degradation products include the fructosyl valine (Fru-Val) and fructosyl valine histidine (Fru-Val-His) or even longer-chain functosyl peptides, which are cleaved from the amino-terminal end of the beta chain of glycated haemoglobin. The fructosyl amino acid or fructosyl peptide is oxidised by the activity of the enzyme fructosyl amino acid oxidase (FAOX) or the enzyme fructosyl peptide oxidase (FPOX), wherein a result of that oxidation step is the production of hydrogen peroxide ($H_2O_2$).

The amount of hydrogen peroxide produced in the above-mentioned oxidation step correlates with the amount of fructosylated amino acid or peptide. Accordingly the amount of hydrogen peroxide produced in this step is a measurement in respect of the amount of HbA1c in the sample. Therefore, determination of the amount of HbA1c can ultimately be effected by quantifying the amount of hydrogen peroxide, for example on the basis of a colour reaction which is to be evaluated photometrically and which stoichiometrically correlates with the amount of hydrogen peroxide. In principle however it is also possible to correspondingly use any other analysis method for quantifying the amount of hydrogen peroxide in a sample.

In a given method of quantifying hydrogen peroxide, a reduced leuco dye is oxidised with hydrogen peroxide. That method however entails the difficulty that autooxidation of the leuco dye causes a non-specific blank value signal and an increase in the spectral background which causes difficulty in precise photometric measurement of the analyte signal. On the other hand leuco dyes have the advantage over other dyes that they usually have higher molecular absorption coefficients. In addition for the major part leuco dyes have such high absorption maxima that optical influencing by interaction with constituents of the blood like for example bilirubin and haemoglobin can generally be disregarded.

BRIEF DESCRIPTION OF THE DRAWINGS

FIG. 2A is for TruCal HbA1c Level 1 without addition; FIG. 2B is for TruCal HbA1c Level 1 with addition; FIG. 2C is for low HbA1c, medium haemoglobin without addition; and FIG. 2D is for low HbA1c, medium haemoglobin with addition.

OBJECT OF THE INVENTION

Figure 1:
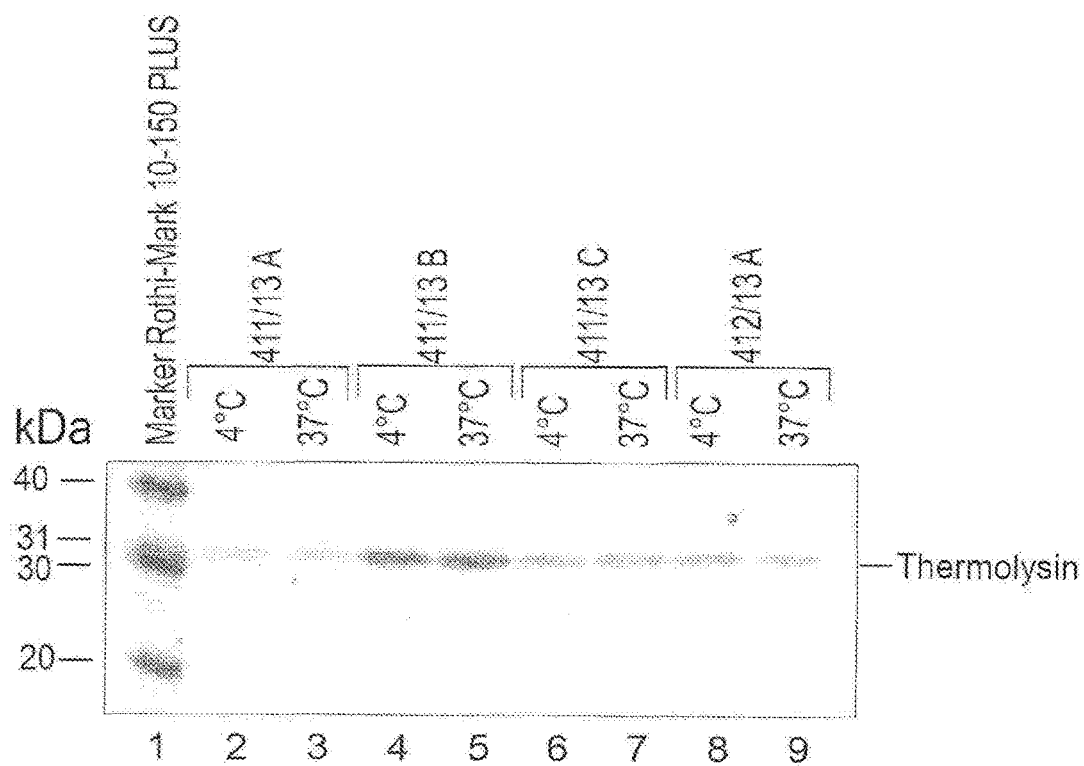
FIG. 1 is a photograph of an SDS-PAGE gel stained with Coomassie staining. The gel was run with four batches of the reagent kits stored at 4° C. and 37° C., respectively, over seven days. Table 1 provides additional information on the batches analyzed.
Figure 2A:
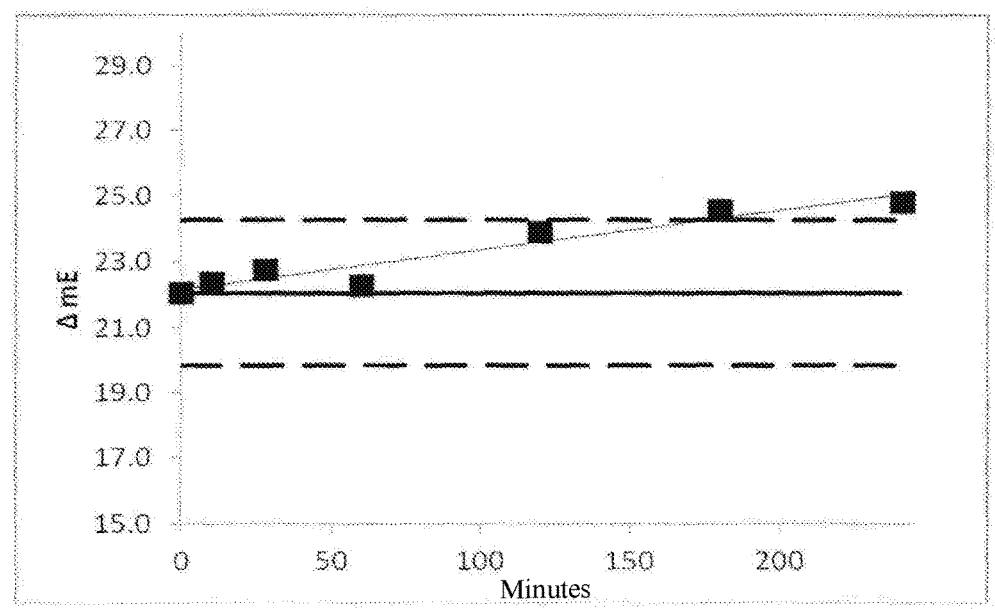
FIGS. 2A, 2B, 2C, and 2D show the results of experiments directed to the stabilization of the unfolded haemoglobin by means of adding a stabilizer to a haemolized blood sample.
Figure 2B:
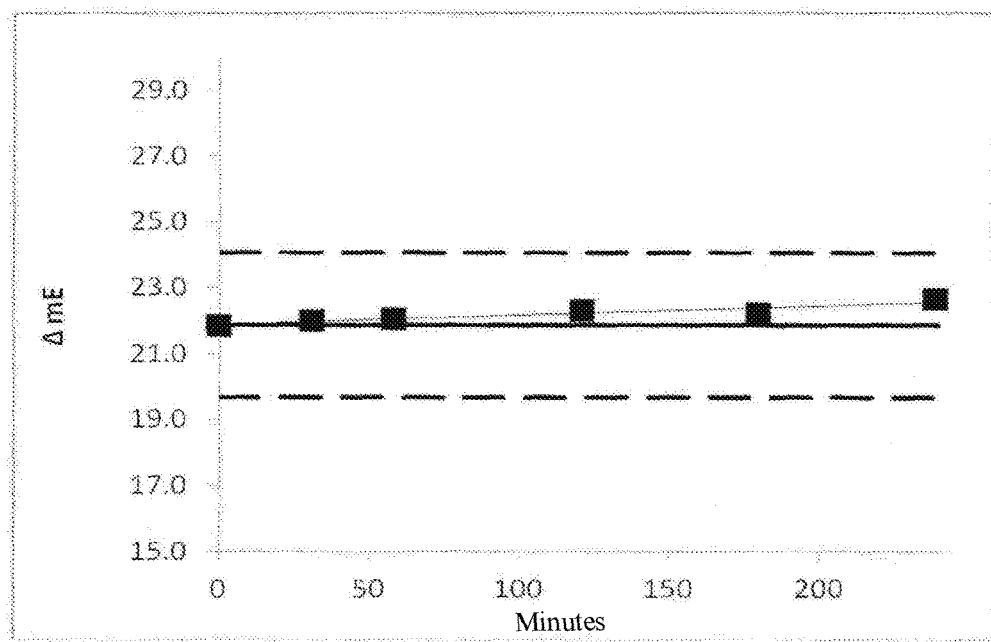
Figure 2C:
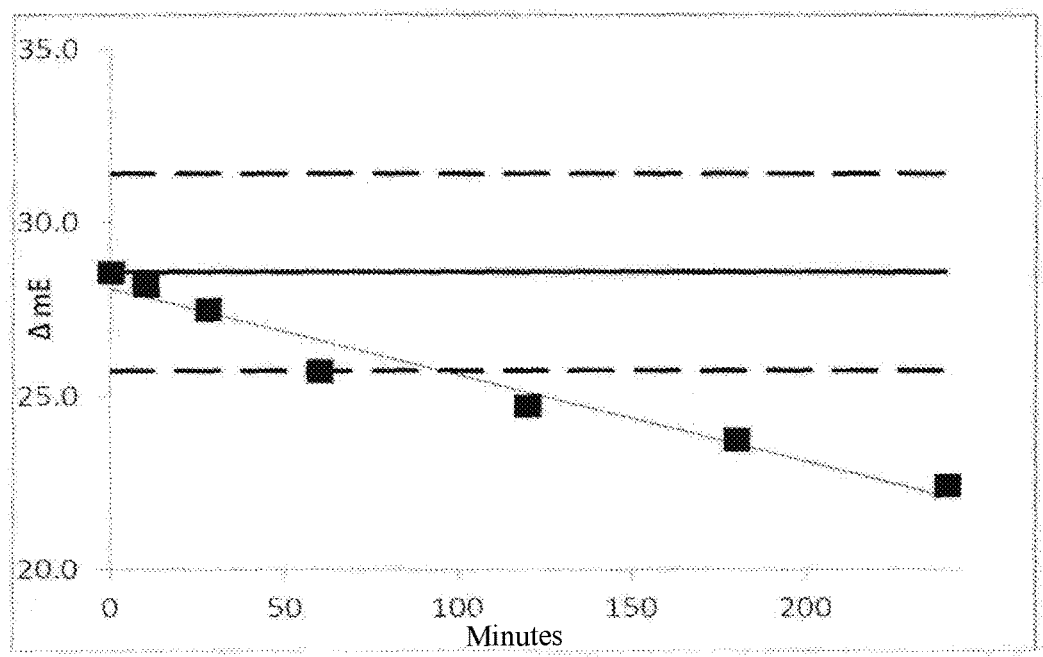
Figure 2D:
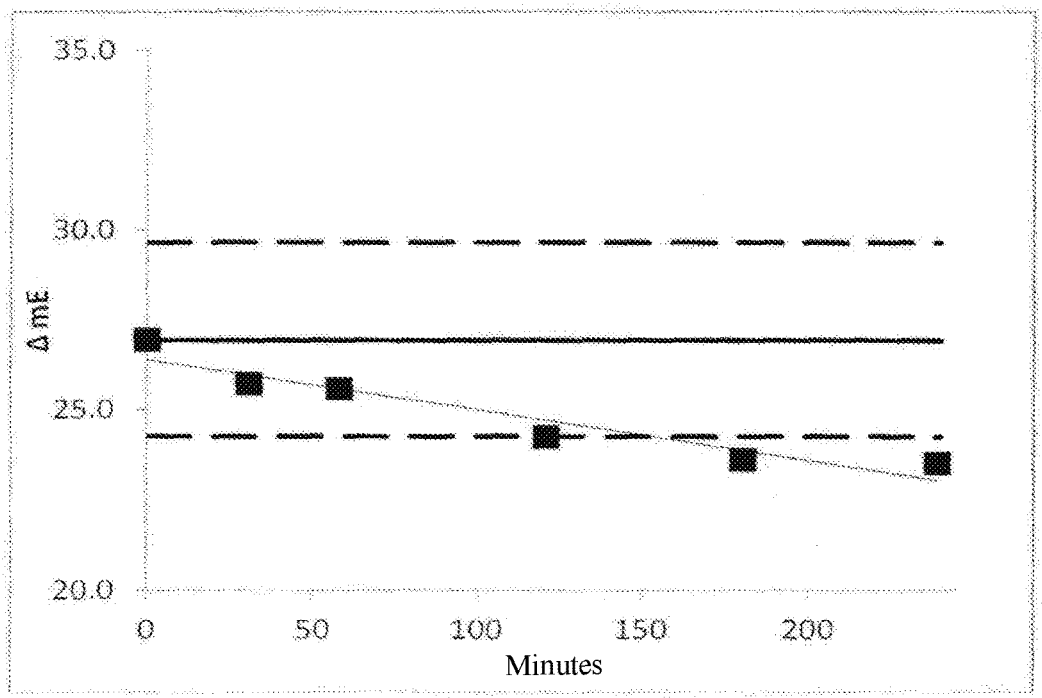

The long-term stability of chemical and diagnostic reagents is a problem which is difficult to resolve, in particular if the reagents are exposed to particularly high or particularly low temperatures and/or significant temperature changes during transport, storage and/or processing. It will be appreciated that this also applies to the same extent as for the above-discussed leuco dyes, for the enzymes and other reagents used in HbA1c tests.

At the same time however it is also of not immaterial importance for the stability of the starting material which is to be to be investigated as well as that of the intermediate and end products of the reaction to be ensured to achieve reliably reproducible results.

Therefore the inventors of the present application set themselves the object of providing a method of determining the amount of glycated haemoglobin (HbA1c) in a sample and reagents which can be used in that respect, in which the chemical compounds essential to the reaction are present in sufficiently stable form. Preferably the aim of the method according to the invention and the reagents according to the invention is to permit total haemoglobin determination at the same time as determining the amount of HbA1c.

DESCRIPTION OF THE INVENTION

In accordance with the invention the above-described object is attained by various aspects which are described in detail hereinafter and which usually have the common denominator that they comprise a method of determining the amount of HbA1c in a sample, in which the following method steps are performed:

a) haemolysis of the erythrocytes in the sample to release the haemoglobin, including HbA1c contained therein, b) bringing the haemoglobin, including HbA1c, released in method step a) into contact with a proteolytically acting agent for producing glycated haemoglobin degradation products, and c) determining the amount of HbA1c by quantification of the glycated haemoglobin degradation products produced in method step b).

The term sample is used in connection with the present invention to denote any material which is prepared for the purposes of the analysis operation and which contains a proportion to be analysed of haemoglobin and/or HbA1c. In most cases the sample will be a sample of fresh whole blood. The present invention however also embraces such samples like for example blood preserves, purified blood, whole blood lyophilisate, erythrocytes concentrate, pre-haemolysed blood samples, haemoglobin standard solutions, HbA1c standard solutions and standard solutions which contain synthetic haemoglobin degradation products like for example synthetic HbA1c degradation products.

Insofar as the HbA1c is already present free in the sample to be analysed method step a) is not required. In the case of standard solutions which contain synthetic haemoglobin or HbA1c degradation products method step b) is in addition also not required. Insofar as the haemoglobin or the HbA1c inherently contained therein or degradation products thereof are not already present in solution in the sample to be analysed they are put into a usually aqueous solution prior to or during step a).

Haemolysis of the erythrocytes can basically be effected with all mechanical, chemical or osmotic haemolysis means or methods, of which the man skilled in the art knows that they lead to complete haemolysis of the erythrocytes. One means or method in accordance with the present invention is deemed to be haemolytically acting when it leads to dissolution of the erythrocytes by destruction of the cell membrane and transfer of the haemoglobin contained in the erythrocytes into the ambient medium.

Examples of haemolytically acting means or methods which are known to the man skilled in the art are ultrasound treatment or the addition of haemolytic detergents or strongly hypotonic salt solutions.

In the embodiments of the invention in which haemolytically acting detergents are used they can be selected for example from ionic, anionic and ampholytic detergents, wherein the term detergent is used here to mean that this embraces substances which reduce the surface tension of a liquid or the interfacial tension between two phases.

In certain embodiments the haemolytically acting detergents used are selected for example from the following: haemolytic polyethylene glycols (PEGs), haemolytic glycosides and esters, haemolytic polyoxyethylene alkyl ethers, haemolytic polyoxyethylene alkyl phenyl ethers, haemolytic polyoxyethylene glycol, haemolytic polyoxypropylene polyoxyethylene triblock copolymers (poloxamers, pluronics), n-dodecyl-β-D-maltoside, n-heptyl-β-D-thioglycoside, n-octyl-β-D-thioglycoside, saccharose laureate, saccharose caprate, saccharose linolate, saccharose palmitate, saccharose cholate and derivatives of the above-mentioned compounds and mixtures thereof.

In principle all proteolytically acting means known to the man skilled in the art fall to be considered like for example proteases, wherein a means in accordance with the present invention has a proteolytic effect when it leads to cleaving of proteins by hydrolysis of the peptide bonds.

In the embodiments in which the proteolytic agent is a protease, it in principle can be selected from all proteases obtained recombinantly from eukaryotes or prokaryotes or obtained endogenously from organisms or organism constituents from serine, threonine, cysteine, asparagine, metal or unknown type, like for example acrosin, aminopeptidase B, bromelain, calpain I, carboxypeptidase A, cathepsin A, cathepsin B, cathepsin D, cathepsin E, cathepsin K, chymotrypsin, collagenase, dipeptidyl peptidase 4, dispase, elastase, factor IIa, factor Xa, ficin, gpr-endopeptidase, HIV-protease, kallikrein, MBTPS1, bromelain, papain, pepsin, plasmin, prepilin type IV peptidase, prolyl-oligopeptidase, proteinase K, proteasom, renin, seccretases (alpha-, beta- and gamma-secretase), thermolysin (EC 3,4,24,27), thrombin, trypsin, urokinase, protease N from *Bacillus* sp., protease P from *Aspergillus* sp., protease XIV from *Streptomyces* sp, and protease S from *Bacillus stearothermophilus*.

In certain embodiments of the invention there can be a related advantage in using proteases which specifically cleave HbA1c. In general the present invention however does not require any specificity of the protease in regard to differentiation between glycated and non-glycated haemoglobin. In that respect therefore it is also possible to use such proteases which do not specifically distinguish between HbA1c and non-glycated haemoglobin. In many embodiments it may even be explicitly desired for a protease to be used, which does not act specifically in a corresponding fashion.

In many aspects of the present invention there is no need for the protease used to lead to given degradation products. In many embodiments of the invention however a protease is specifically used, whose proteolytic activity leads to the release of fructosyl valine histidine or fructosyl valine from the amino-terminal end of the beta chain of glycated haemoglobin.

Determining the amount of HbA1c can basically be effected by all quantification procedures, known to the man skilled in the art, for the glycated haemoglobin degradation products produced in method step b), like for example by an HPLC analysis or enzymatic determination, as was described hereinbefore.

Besides the above-described method the present invention also proposes reagent kits for use in a method of determining the amount of HbA1c in a sample, which are characterised in that they comprise at least two different solutions in separate containers, wherein the at least two different solutions are respectively of such a composition that the various aspects of the invention described in detail hereinafter are implemented.

Aspect 1—Stabilisation of the Protease

In accordance with a first aspect the above-described object of the invention is attained in that there is proposed a method of determining the amount of HbA1c in a sample, in which—insofar as required—method steps a) to c) are performed.

In accordance with the present aspect of the invention the proteolytically acting agent used in method step b) is activated in that at least two different solutions are brought into contact with the HbA1c, wherein the one solution has a pH-value in the range of 1 to 8, and contains i) at least one protease, ii) per 1000 kU/l of protease 0.1 to 2 mmol/l of a chelator respectively for divalent metal ions, and iii) 0.5 to 10 mmol/l $Ca^{2+}$ or 0.5 to 10 mmol/l $Mg^{2+}$, wherein the molar ratio of chelator:$Ca^{2+}$ or chelator:$Mg^{2+}$ is in the range of 1:2 to 1:20 and the other solution contains 100 to 5000 μmol/l of a divalent metal ion selected from $Fe^{2+}$, $Mn^{2+}$, $Co^{2+}$ and $Zn^{2+}$.

In addition there is proposed a reagent kit for use in a method of determining the HbA1c in a sample, which is characterised in that the reagent kit includes at least two different solutions in separate containers, wherein the one solution has a pH-value in the range of 1 to 8 and contains the above-mentioned components i) to iii), wherein the molar ratio of chelator:$Ca^{2+}$ or chelator:$Mg^{2+}$ is in the range of 1:2 to 1:20 and the other solution contains 100 to 5000 µmol/l of a divalent metal ion selected from $Fe^{2+}$, $Mn^{2+}$, $Co^{2+}$ and $Zn^{2+}$.

In certain embodiments of the invention the pH-value of the solution containing the protease is at least 4 and/or at most 6. In other embodiments of the invention the pH-value of the solution containing the protease is greater than 4 and/or less than 6. In a specific embodiment of the invention the pH-value of the solution is in the range of 4.5 to 5.5 and in very specific embodiments it is in the range of 4.9 to 5.1.

The activity of the metalloproteases depends on the presence of divalent metal ions like $Fe^{2+}$, $Mn^{2+}$, $Co^{2+}$ or $Zn^{2+}$. At the present time 54 metalloprotease families are divided into 15 clans, wherein outstanding significance is attributed to the clan MA with 39 families. Just 19 of those 39 families can be associated with the so-called neutral zinc metalloprotease. The other metalloprotease are manganese- or cobalt-dependent.

Inter alia the following metalloproteases belong to the clan MA: membrane alanyl aminopeptidase, peptidyl-dipeptidase A, thimet-oligopeptidase, oligopeptidase F (*Lactococcus*), mycolysin, Immune-Inhibitor A (*Bacillus*), no neutral *streptomyces*-protease, leishmanolysin, microbial collagenase, collagenase colA, matrix-metallopeptidase 1, serralysin, fragilysin, autolysin (*Chlamydomonas*), astacin, reprolysin, neprilysin, IgA-specific metalloendopeptidase, t entoxilysin, t hermolysin, neutral *staphylococcus*-protease, carboxypeptidase t aq, lethal anthrax-factor, deuterolysin, fungalysin, cell cleaving protein ftsH, cytophagalysin, pappalysin 1, Ste24-endopeptidase (*Saccharomyces*), HtpX-endopeptidase (*E. coli*), archaelysin, peptidase blaR1, peptidase prtB, enhancin, glycyl-aminopeptidase (*Sphingomonas capsulate*), peptidase IgA (*Clostridium ramosum*), peptidase stcE (*E. coli*), peptidyl-asp-Metalloendopeptidase (*P. aeruginosa*) and ImmA-peptidase.

If proteases are in their active form over a prolonged period there is the risk that significant proportions of the enzyme are destroyed by self-digestion. In that respect temporary inactivation of the enzymatic activity of proteases is frequently wanted if self-digestion of the enzyme is to be avoided.

The problem of self-digestion of proteases is already known per se in the state of the art. To resolve that problem the state of the art proposed for example for the protease thermolysin removing zinc from the theremolysin by chelators, in particular SH group-containing reagents, or by a simple excess of EDTA.

The inventors of the present application realise however that the excess of chelator can have a negative influence on the stability of the protease as the chelator not only removes from the protease the cofactor essential for catalytic activity—as is desired—but also to a significant proportion $Ca^{2+}$ and/or $Mg^{2+}$, although the stability and structural integrity of many proteases requires the presence of $Mg^{2+}$ or $Ca^{2+}$. In addition the inventors found that the preparation of the protease in its inactive form in a reagent compartment at a specific pH-value and reactivation of the protease by means of a divalent metal ion selected from $Fe^{2+}$, $Mn^{2+}$, $Co^{2+}$ and $Zn^{2+}$, which is prepared in a second reagent compartment, represents the best form of long-term storage of the protease without significant activity losses.

As calcium or magnesium ions are of essential significance for the stability of the protein structure of the protease the use of an excess of chelator consequently causes destabilisation of the protease protein. The inventors however found that it is possible to counteract such destabilisation by providing a considerable excess of $Ca^{2+}$ and/or $Mg^{2+}$, which provides that use of the chelator in the amount required for deactivation of the protease does not entail destabilisation of the protein structure of the protease.

What is crucial in this connection is in particular the molar ratio of the calcium or magnesium ions used in relation to the amount of chelator used, as that ensures that there are sufficient calcium or magnesium ions to stabilise the protein structure of the protease without in that respect displacing the divalent metal ions selected from $Fe^{2+}$, $Mn^{2+}$, $Co^{2+}$ and $Zn^{2+}$ from the chelate complex with the chelator.

Examples of chelators for divalent metal ions, that are suitable in accordance with the present invention, are acetylacetone, nitrilotriacetic acid (NTA), ethylenediamine, ethylenediamine tetraacetate (EDTA), N-(2-hydroxyethyl)-ethylenediamine-N,N,N'-triacetic acid trisodium salt (HEDTA), cyclohexanediamine tetraacetic acid (CDTA), ethylene glycol-bis(aminoethylether)-N,N,N',N' tetraacetic acid (EGTA), 2-(2-aminoethylamino)ethanol, diethylenetriamine, iminodiacetate, triethylenetetramine, triethylentetraminhexaacetic acid (TTHA), triaminotriethylamine, nitrilotriacetat, bis(salicylidene)ethylenediamine, ethylenediaminotriacetate, ethylenediamintetraacetate, diethylenetriaminepentaacetate (DTPA), 1,4,7,10-tetraazacyclododecane-1,4,7,10-tetraacetate, oxalate, tartrate, citrate, dimethylglyoxime, 8-hydroxychinoline, 2,2'-bipyridine, 1,10-phenanthroline, dimercaptosuccinic acid, 1,2-bis(diphenylphosphino)ethane.

The chelator used for the divalent metal ions selected from $Fe^{2+}$, $Mn^{2+}$, $Co^{2+}$ and $Zn^{2+}$ binds with higher affinity to divalent metal ions selected from $Fe^{2+}$, $Mn^{2+}$, $Co^{2+}$ and $Zn^{2+}$ than to calcium or magnesium ions. Preferably the chelator used binds with an at least $10^3$-times higher binding strength to divalent metal ions selected from $Fe^{2+}$, $Mn^{2+}$, $Co^{2+}$ and $Zn^{2+}$ in comparison with calcium or magnesium ions.

The chelator concentration can be freely selected within the above-specified range in dependence on the amount of protease. In an embodiment the solution contains 0.5 to 1.5 mmol/l of chelator per 1000 kU/l of protease. In another embodiment the solution contains 0.9 to 1.1 mmol/l of chelator per 1000 kU/l of protease.

The amount of calcium or magnesium ions can also be freely selected in the above-mentioned ranges of concentration. In an embodiment the calcium or magnesium ion concentration is in the range of 3 to 8 mmol/l. In another embodiment the calcium or magnesium concentration is in the range of 4 to 7 mmol/l.

The metal ions can be used in the reagent solution employed in any suitable salt form as long as the selected salt form affords the required amount of dissolved metal ion in the batch like for example chlorides, nitrates, sulphates, formiates and acetates. In the embodiments in which the metal ion $Ca^{2+}$ or $Mg^{2+}$ is made available in the batch the calcium or magnesium salt which is present for that purpose in the reagent solution used is in certain embodiments therefore calcium chloride, nitrate, formiate, acetate or the respective $Mg^{2+}$ salt. In the embodiments in which the divalent metal ion is selected from $Fe^{2+}$, $Mn^{2+}$, $Co^{2+}$ and $Zn^{2+}$ the metal salt provided for that purpose in the reagent solution used can be for example iron chloride, manganese nitrate, cobalt formiate or zinc acetate.

The molar ratio of chelator:$Ca^{2+}$ or chelator:$Mg^{2+}$ can be freely selected in the range of 1:2 to 1:20 depending on the respective embodiment. In certain embodiments of the present invention the molar ratio of chelator:$Ca^{2+}$ and chelator:$Mg^{2+}$ is in the range of 1:4 to 1:10. In many embodiments the ratio of chelator:$Ca^{2+}$ and chelator:$Mg^{2+}$ is in the range of 1:4 to 1:8. In other embodiments the ratio is inn the range of 1:5 to 1:7.

Reactivation of the protease inactivated in the above-described manner is effected in accordance with the invention by the addition of a solution with 100 to 5000 μmol/L of the metal ion which is essential for enzymatic activity of the respectively used protease ($Fe^{2+}$, $Mn^{2+}$, $Co^{2+}$ or $Zn^{2+}$). The inventors of the present application found that this specific amount of the respective divalent metal ions is sufficient to reoccupy the sites in the protein structure of the protease, that are required for activation of the protease, in spite of the simultaneously present significant amounts of chelator and calcium or magnesium ions. The metal ion content of the activation solution can be freely selected in the specified range depending on the respective embodiment involved. In certain embodiments the metal ion content is in the range of 500 to 2000 μmol/L. In other embodiments the metal ion content is in the range of 200 to 400 μmol/l.

In an embodiment of the present invention the solution which contains one of the divalent metal ions selected from $Fe^{2+}$, $Mn^{2+}$, $Co^{2+}$ and $Zn^{2+}$ is a haemolysis solution which is added to the sample in method step a), that haemolysis solution containing a haemolytic detergent. More specifically one of the objects of the present invention is also that of combining together as many as possible of the reagents used in the HbA1c determination operation into as few as possible combined reagent solutions. In this connection it has been found that the divalent metal ions which are selected from $Fe^{2+}$, $Mn^{2+}$, $Co^{2+}$ and $Zn^{2+}$ and which are required for later activation of the protease can certainly also be present in another reagent solution than in that which contains the protease. For example in many embodiments of the invention the divalent metal ions selected from $Fe^{2+}$, $Mn^{2+}$, $Co^{2+}$ and $Zn^{2+}$ are also present in the solution with which the FPOX or the FAOX is supplied (see below R1) or also in the haemolysis solution which was also used right at the beginning of the HbA1c analysis procedure.

In an embodiment of the present invention the various reagents used in HbA1c determination are brought together in the form of the following solutions which are provided in separate containers:
  a haemolysis solution (H) containing a haemolytic detergent and 100 to 5000 μmol/L of a divalent metal ion selected from $Fe^{2+}$, $Mn^{2+}$, $Co^{2+}$ and $Zn^{2+}$,
  a first reagent solution (R1) containing FPOX or FAOX and peroxidise, and
  a second reagent solution (R2) additionally containing the protease and per 1000 kU/l of protease 0.1 to 2 mmol/l of a chelator for divalent metal ions and 1 to 10 mmol/l of $Ca^{2+}$ or $Mg^{2+}$, wherein the molar ratio of chelator:$Ca^{2+}$ and chelator:$Mg^{2+}$ respectively is in the range of 1:2 to 1:20, and a leuco dye.

The above-mentioned reagent kit can be used in a method of HbA1c determination in the following manner. Firstly—insofar as is required—sample preparation is effected, in which whole blood is mixed with the haemolytic solution. The first reagent solution (R1) is then added to the haemolysate resulting therefrom, the result of this being that the FPOX contained in the first reagent solution already breaks down endogenous fructosyle peptides possibly present, but not the terminal fructosylated peptides which are relevant to HbA1c determination as they are not yet released.

After the reaction is substantially concluded photometric determination of the total haemoglobin content of the pre-incubated haemolysate is effected. Actual incubation is then effected, in which the second reagent solution (R2) is added to the pre-incubated haemolysate. The protease apo enzyme contained therein (for example thermolysin apo enzyme) is activated by the additional divalent metal ions (for example zinc ions) already contained in the composition by way of the haemolysis solution and cleaves inter alia N-terminal glycated peptide from the beta chain of the haemoglobin. The cleaved glycated peptide is then reacted by the FPOX, wherein hydrogen peroxide is produced upon cleaving of the glycated peptide into peptide and glucosone.

The peroxidase already introduced into the composition by way of the first reagent solution (R1), in the presence of the resulting hydrogen peroxide, causes oxidation of the leuco dye towards its coloured oxidation form. The actual HbA1c determination operation can then be effected by photometric measurement for example very quickly (for example 10 to 30 seconds, depending on the nature of the measuring instrument) after addition of the second reagent solution (R2), that is to say immediately before the FPOX-induced reaction occurs, and once again at a later time (for example 2 to 15 minutes, depending on the respective nature of the measuring instrument) after the addition of R2, that is to say after conclusion of the hydrogen peroxide-induced oxidation of the leuco dye. Ultimately, determination of the HbA1c content is effected in consideration of the difference between the two measurements and by formation of the quotient from the contents of HbA1c and the previously determined total haemoglobin. The measurement intervals however are very heavily dependent on the respectively employed analyser, photometer and so forth. Accordingly only one direct measurement after 2 to 15 minutes would also be possible.

Aspect 2—Stabilisation of the Unfolded Haemoglobin

Besides stabilisation of the protease the inventors of the present invention also set themselves the object of being able to unfold the haemoglobin contained in a sample, including HbA1c, as greatly as possible, and stabilise it in that unfolded form in order for example to permit digestion of the utmost efficiency of the haemoglobin by a protease and to put the haemoglobin into a measurable photometrically stable form.

It is known from the state of the art that haemoglobin is unfolded to a certain degree by the reduction in pH-value in the haemolycate. In the conventional methods of determining the amount of HbA1c unfolding is effected at a pH-value of about 5. A greater reduction in the HbA1c value however has the disadvantage that the haemoglobin treated in that way is severely denatured and agglutinated and precipitates in that form so that it is no longer available in a suitable form for digestion with a protease.

The inventors of the present invention however found a way in which, with a very low pH-value, extremely rapid and efficient unfolding and subsequent stabilisation of the unfolded haemoglobin can be achieved. For that purpose in accordance with this aspect of the invention there is proposed a method of determining the amount of HbA1c in a sample, in which—insofar as is required—method steps a) to c) are performed, wherein that method is characterised in that the haemolysis in method step a) is effected by adding a haemolysis solution (H), wherein that haemolysis solution has a pH-value in the range of 1 to 3, and contains a haemolytic detergent and at least one stabiliser, wherein the at least one stabiliser is selected from a phosphatidylcholine, 2-(methacryloyloxyethyl)-2'-(trimethyl ammoniumethyl) phosphate polymer or copolymer or mixtures thereof.

The term phosphatidylcholine is used here to denote a compound of the general formula (I):

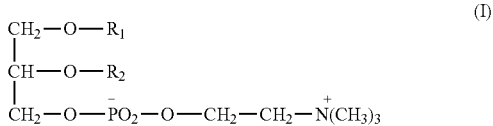

wherein $R_1$ and $R_2$ are selected from completely saturated or singly or multiply unsaturated straight-chain or branched-chain fatty acid residues. In the embodiments with multiply unsaturated fatty acid residues they are preferably doubly, trebly or quadruply unsaturated and in certain embodiments independently of the degree of saturation the fatty acid residues are selected from those with a chain length in the range of C8 to C22 or those with a chain length in the range of C16 to C22 (for example 1,2-dioleoyl-sn-glycero-3-phosphocholine).

The term 2-(methacryloyloxyethyl)-2'-(trimethyl ammoniumethyl)phosphate polymer or copolymer is used here to denote a polymer or copolymer with recurrent units of the general formula (II):

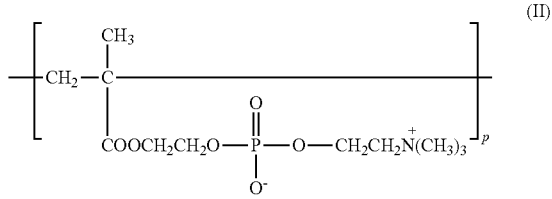

In the embodiments which are present in the form of copolymers they include, besides the units with the above-specified general formula (II), they include further methacrylate units which are esterified with aliphatic or aromatic residues.

After the addition of the haemolysis solution the pH-value of the haemolysate corresponds to that of the haemolysis solution. That is achieved by suitable buffering of the haemolysis solution. As in accordance with the present aspect of the invention the haemolysis solution has a pH-value in the range of 1 to 3, the pH-value of the haemolysed sample (=haemolysate) is thus also set to a pH-value in the range of 1 to 3. The constantly low pH-value of the haemolysate in conjunction with the stabilising detergents has the result that the unfolded haemoglobin can be quickly and efficiently broken down.

In addition there is proposed a reagent kit for use in a method of determining the amount of HbA1c in a sample, wherein the reagent kit includes at least one haemolysis solution which has a haemolytically acting detergent and in addition 2-(methacryloyloxyethyl)-2'-(trimethyl ammoniumethyl) phosphate polymer, a phosphatidylcholine or mixtures thereof and has a pH-value in the range of 1 to 3.

The reduction of the pH-value into the range of 1 to 3 leads to very rapid and strong unfolding of the haemoglobin. However, as was already mentioned hereinbefore, there is the risk that the haemoglobin is denatured, agglutinated and precipates, as can also be effected for example by adding trichloroacetic acid. The inventors of the present application however found that it is possible to avoid denaturing, precipitation and agglutination of the haemoglobin if the haemolysis solution additionally contains 2-(methacryloyloxyethyl)-2'-(trimethyl ammoniumethyl), a phosphatidylcholine or mixtures thereof.

In connection with this aspect of the invention the term "unfolding" is used to denote partial dissolution of the secondary and tertiary structures, which however does not lead to precipitation of the haemoglobin. The haemoglobin which is unfolded in accordance with the present invention therefore remains in solution in contrast to denatured haemoglobin. The term denatured haemoglobin is used in accordance with this invention therefore to denote such haemoglobin whose protein structure was dissolved to such an extent that the protein precipitates and agglutinates, as is effected for example by treatment with tricholoroacetic acid.

The above-described great unfolding of the haemoglobin with at the same time stabilisation of the unfolded product occurs surprisingly rapidly within only 5 to 15 seconds and that effect can be achieved in the presence of 2-(methacryloyloxyethyl)-2'-(trimethyl ammoniumethyl)phosphate polymer, a phosphatidylcholine or mixtures thereof in the entire claimed pH-value range of 1 to 3. In certain embodiments of the invention the pH-value is in the range of 2 to 3. In an embodiment the pH-value of the haemolysis solution is in the range of 2.4 to 2.6.

Aspect 3—Stabilisation of the Leuco Dye

A further object that the inventors of the present application set themselves is stabilisation of the leuco dye in the methods of determining the amount of HbA1c in a sample, in which such a leuco dye is used.

The term leuco dye is used here to denote a substance which, by reaction with at least one oxidising substance and/or a substance with peroxidase activity is converted from a colourless leuco starting form into a photometrically measurable coloured form. Examples of leuco dyes suitable for the present invention are N,N,N',N',N'',N''-hexa(3-sulphopropyl)-4,4',4''-triaminotriphenyl methane hexasodium salt (TPM-PS), N-(carboxymethylaminocarbonyl)-4,4'-bis(dimethylamino)-diphenylamine sodium salt (DA64), 10-(carboxymethylaminocarbonyl)-3,7-bis(dimethylamino)-phenothiazine sodium salt (DA67), 2,2'-azinobis(3-ethylbenzothiazoline-6-sulphonic acid (ABTS) and triphenylamine, phenothiazine, phenoxazine, benzidine, triallylimidazole, o-phenylene diamine derivatives, triphenylmethane and o-tolidine derivatives with the above-mentioned properties of a leuco dye and combinations of 4-aminoantipyrine and a phenol compound or an N,N-disubstituted aniline compound and combinations of 3-methylbenzothiazolinone hydrozone (MBTH) and an aniline compound. Further examples of leuco dyes suitable for the present invention are the diphenylamine derivatives described in EP0038205, EP0124287 and EP0045220.

In an aspect of the present invention stabilisation of the leuco dye is effected in the method of determining the amount of HbA1c in a sample in that, in the method method steps a) to c) are performed, and quantification of the glycated haemoglobin degradation products is effected in method step c) by oxidation thereof by means of FPOX or FAOX with the production of hydrogen peroxide and by determining the resulting amount of hydrogen peroxide, wherein the amount of hydrogen peroxide is quantified on the basis of the colour reaction of a leuco dye in the presence of a peroxidase, and wherein the leuco dye is produced in a solution which for stabilisation of the dye contains a compound of the general formula (I):

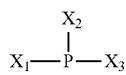

wherein P stands for a phosphorus atom and wherein $X_1$, $X_2$ and $X_3$ are selected independently of each other from substituted or unsubstituted straight-chain or branched-chain $C_1C_8$-alkyl residues, substituted or unsubstituted cyclohexyl residues and substituted or unsubstituted phenyl residues.

As was already mentioned in the opening part of this specification the principle of leuco dyes is based on the fact that detection of a substance is effected by way of the leuco dye converting from its colourless leuco starting form into a colour form by virtue of the presence of the substance to be detected. To ensure that that conversion does not already occur prior to implementation of the actual detection reaction it is advantageous if the leuco dye is stabilised in its colourless reduced form without the actual detection reaction being adversely influenced thereby.

The inventors of the present application found that effective stabilisation of leuco dyes can be achieved by the addition of compounds of the general formula (I) without the actual detection reaction (in the present case detection of hydrogen peroxide in the presence of the enzyme peroxidase) being adversely effected or damaged thereby.

Examples of compounds of the general formula (I) are tris(2-carboxyethyl)phosphatin (TCEP), bis(p-sulphonatophenyl)phenylphosphine dihydrate dipotassium salt, 1,3,5-triaza-7-phosphine adamantane, tris(3-sulphonatophenyl)phosphine hydrate sodium salt, tris(4,6-dimethyl-3-sulphonato-phenyl)phosphine trisodium salt hydrate, tris(hydroxymethyl)phosphine, di-t-butyl(3-sulphonatopropyl)phosphine, diphenyl(m-sulphonatophenyl)phosphine dihydrate sodium salt, and [2-dicyclohexylphosphino)ethyl]-trimethyl ammonium chloride without the intention being that the invention is to be carried out only with those compounds which are only listed by way of example.

Alternatively for stabilising the leuco dye it is also possible to add thio compounds, more especially single ones or a plurality of thioalcohols, thioethers, thioketones or mixtures thereof. Examples of such thio compounds are thiodiglycol, thiomalic acid, thionicotinamide, thio-NAD and mixtures thereof without any limitation of the invention being intended thereby as a result of specifying those examples.

The above-mentioned thio compounds can be used either alone or in combination with the compounds referred to hereinbefore of general formula (I). Accordingly in certain embodiments of the invention the leuco dye is produced in a solution which for stabilisation of the dye contains at least one compound of the general formula (I) like for example TCEP and at least one thio compound like for example thiodiglycol.

Accordingly the present invention also concerns a reagent kit for use in a method of determining the amount of HbA1c in a sample, which is characterised in that it includes at least one reagent solution which contains a leuco dye and for stabilisation of the leuco dye at least one compound of the general formula (I) and/or at least one thio compound.

In an embodiment the concentration of the stabiliser compound of the general formula (I) is in the range of 10 to 20 mol per mol of leuco dye contained in the reagent solution. In special embodiments the amount of stabiliser compound of the general formula (I) is in the range of 10 to 15 mol per mol of leuco dye.

In the above-described method of determining the amount of HbA1c in a sample reagents are frequently used, which contain SH groups like for example the above-mentioned thio compounds. Such SH group-containing compounds can however interfere with the actual HbA1c detection reaction and more specifically at the site at which FPOX or FAOX reacts the fructosylated amino acids or peptides forming hydrogen peroxide and the hydrogen peroxide resulting therefrom is quantified. In that respect the inventors of the present application have shown that SH groups which cause disturbance in the above-mentioned detection reaction must be blocked as much as possible.

According to the invention it is therefore proposed, for optimisation of the actual HbA1c detection reaction, that the SH groups which disturb that reaction are blocked by the addition of an SH group-trapping agent like for example N-ethylmaleinimide (NEM). The addition of the SH group-trapping agent should accordingly occur at latest immediately prior to carrying out the HbA1c detection reaction.

In a given embodiment the SH group-trapping agent, for example NEM, is contained in the haemolysis solution. In an alternative embodiment the SH group-trapping agent, for example NEM, is contained in a reagent solution which is kept separately from the reagent solution and is added, in which there is a leuco dye stabilised with thioalcohols.

Insofar as is desired, the method according to the invention can also be carried out in such a way that the total haemoglobin concentration is determined during or between method steps a)-c). Accordingly the method preferably includes a step for determining the total haemoglobin concentration in order to be able to specify the HbA1c concentration directly as a relative amount, for example in mmol/mol.

Special Embodiments of the Reagent Kits

In an embodiment of the invention described in the present application there is provided a reagent kit which includes at least the following three solutions in separate containers:

a haemolysis solution (H) containing a haemolytically acting detergent,
a first reagent solution (R1) containing FPOX or FAOX, and
a second reagent solution (R2) containing a protease,
wherein:
a) the haemolysis solution (H) has a pH-value in the range of 1 to 3 and 2-(methacryloyloxyethyl)-2-(trimethyl ammoniumethyl)phosphate polymer, phosphatidylcholine or mixtures thereof, and/or
b) the haemolysis solution (H) contains 100 to 5000 µmol/L of a divalent metal ion which is selected from $Fe^{2+}$, $Mn^{2+}$, $Co^{2+}$ and $Zn^{2+}$, and the second reagent solution (R2) contains a protease whose proteolytic activity leads to release of fructosyl-valine-histidine or fructosyl-valine from the amino-terminal end of the beta chain of glycated haemoglobin, and contains per 1000 kU/l of protease respectively 0.1 to 2 mmol/l of a chelator for divalent metal ions and 0.5 to 10 mmol/l of $Ca^{2+}$ or 0.5 to 10 mmol/l of $Mg^{2+}$, wherein the molar ratio of chelator:$Ca^{2+}$ and chelator:$Mg^{2+}$ respectively is in the range of 1:2 to 1:20, and/or
c) the second reagent solution (R2) contains a leuco dye and a proportion of a compound of the general formula (I) for stabilisation of said leuco dye and/or a proportion of at least one thio compound for stabilisation of the leuco dye.

In the embodiments in which quantitative determination of the HbA1c is ultimately effected on the basis of the hydrogen peroxide formed in the detection reaction at least one of the above-mentioned reagent solutions contains a peroxidase and at least another of the reagent solutions contains a leuco dye. In these embodiments selectively one of the reagent solutions also contains an SH group-trapping agent like for example NEM, wherein the SH group-trapping agent is contained in one of the reagent solutions in which the leuco dye is not contained.

In a special embodiment of the present invention the reagent kit comprises three reagent solutions having the following constituents:
- a haemolysis solution containing a haemolytically acting detergent, 2-(methacryloyloxyethyl)-2-(trimethyl ammoniumethyl)phosphate polymer, phosphatidylcholine or mixtures thereof, a metal salt for preparation of a metal ion selected from $Fe^{2+}$, $Mn^{2+}$, $Co^{2+}$ and $Zn^{2+}$ in the previously required amount and an SH group-trapping agent like for example NEM,
- a first reagent solution (R1) containing FPOX or FAOX and peroxidase (POD), and
- a second reagent solution (R2) containing a protease whose proteolytic activity leads to release of fructosyl-valine-histidine or fructosyl-valine from the amino-terminal end of the beta chain of glycated haemoglobin, a $Ca^{2+}$ salt or an $Mg^{2+}$ salt and a chelator for divalent metal ions, each in the above-required amounts, a leuco dye and a compound of the general formula (I) for stabilisation of the leuco dye and/or a thio compound for stabilisation of the leuco dye.

For the purposes of the original disclosure it is pointed out that all features as can be seen by a man skilled in the art from the present description, the drawings and the claims, even if they are described in specific terms only in connection with certain other features, can be combined both individually and also in any combinations with others of the features or groups of features disclosed here insofar as that has not been expressly excluded or technical aspects make such combinations impossible or meaningless. A comprehensive explicit representation of all conceivable combinations of features is dispensed with here only for the sake of brevity and readability of the description.

It is further pointed out that it is self-evident to the man skilled in the art that the embodiments by way of example hereinafter only serve to set forth by way of example the possible embodiments of the present invention, that are set out as examples of the invention. The man skilled in the art will therefore readily understand that all other embodiments which have the features or combinations of features according to the invention as recited in the claims also fall within the scope of protection of the invention. A comprehensive explicit representation of all conceivable embodiments is dispensed with here only for the sake of brevity and readability of the description.

EXAMPLES

1. Stabilisation of the Protease
   a) Stabilisation of the Protease, Analysis by SDS Gel Electrophoresis:

The protease thermolysin, upon storage in liquid form or in reagents over time at 2 to 8° C. or higher temperatures has a strong tendency to break down autoproteolytically. That is a bar to the use of the protease for liquidly stable reagents with a uniform quality requirement over prolonged periods of time. The protease thermolysin is $Zn^{2+}$ dependent and the inventors were able to show that the one protease inactivation by means of chelators with at the same time $Ca^{2+}$-dependent structural stabilisation permits better use of thermolysin and related metalloproteases for clinical-chemical diagnostics.

To prove the possible stabilisation of a protease different respective amounts or ratios of chelator and $Ca^{2+}$ were introduced into a reagent base matrix in which the protease thermolysin was contained. The concentrations of EDTA and calcium, used in that case in the reagent 2, are specified in the following Table 1.

TABLE 1

| Batch | [µmol/L] EDTA | [mmol/L]$Ca^{2+}$ |
| --- | --- | --- |
| E 411/13 A | 12 | 0.6 |
| E 411/13 B | 1000 | 6 |
| E 411/13 C | 12 | 6 |
| E 412/13A | / | 6 |

The resulting batches (see the Table above) were divided up and stored at 4° C. and 37° C. respectively over 7 days. Identical sample amounts were respectively taken from those batches, mixed with SDS-PAGE application buffer and the protein composition was denaturingly separated by way of SDS-PAGE and visualised by Coomassie staining (see FIG. 1).

A markedly greater amount of the protease thermolysin is evidently visible in the bands 4 and 5 in comparison with the other bands of the gel. Accordingly the protease thermolysin is markedly better protected against self-digestion in temperature-independent relationship in that composition, than in the other compositions. Comparison of the batches with the number E411/13B shows that the presence of EDTA is essential for protection from self-digestion. Comparison of the batches with the numbers E411/13A and E411/13C with E411/13B shows that a certain minimum amount of EDTA is required and that the calcium ions must also be present in a given minimum amount.

In addition the following data demonstrate the thermolysin-stabilising action of a specific composition in terms of storage over a prolonged period at 4° C. and 37° C. respectively.

b) Analysis of Stabilisation of the Protease in the HbA1c Test System.

Stabilisation of the protease, shown in FIG. 1 at the protein-analytical level, was implemented by way of example in an HbA1c reagent matrix. For that purpose various combinations of concentrations of calcium ions and EDTA were added to a reagent base matrix 2, with a respective equal amount of the example protease thermolysin. Those batches were respectively divided up, directly measured (fresh) or reagent 2 was stored over 11 days at 2-8° C. (11d/2-8° C.) and reagent 2 was stored over 7 days at 37° C. and then a further 4 more days at 2-8° C. (7d/37° C.+4d/2-8° C.).

Those corresponding reagent base matrices 2 were then measured with a respectively identical haemolysis solution and identical reagents 1 on a BM 6010c clinical-chemical analyser system.

DiaSys Calibrators TruCal HbA1c net (Article 1 3350) were used for calibration. The HbA1c determination of the different reagent matrices 2 was measured and evaluated over time and stored at different temperatures, shown in Table 2. ΔmE in that respect corresponds to the difference in respect of Calibrator Level 2 in relation to Calibrator Level 1 in mE.

The basic compositions forming the basis for measurement were in that respect as follows, wherein in the individual tests individual constituents (calcium acetate/ETDA) were varied in the way specified in the Tables shown hereinafter:

Haemolysis Solution:
Glycine, 60 mol/l
N-ethylmaleimide, 7.5 mmol/L
2-(Methacryloyloxyethyl)-2'-(trimethyl ammoniumethyl) phosphate polymer, 50 g/L
Zinc chloride 1200 μmol/L
pH-value 2.5
Reagent Solution 1:
BIS-TRIS, 100 mmol/L
NaCl, 100 mmol/L
FPOX, greater than 0.8 kU/L
POD, greater than 50 kU/L
pH-value 7.2
Reagent Solution 2:
Sodium acetate, 20 mmol/L
NaCl, 100 mmol/L
Calcium acetate, concentration see Table 2
TCEP, 0.1 mmol/L
DA-67, 0.08 mmol/L
Titriplex/EDTA, concentration see Table 2
Protease (thermolysin) 1000 U/ml
pH-value 5.0

The application on which the measurement was based was in that respect as follows:

| | |
|---|---|
| Reagent 1: | 90 μL |
| Reagent 2: | 30 μL |
| Haemolysated sample: | 15 μL |
| Haemolysis step: | 5 μL sample + 100 μL haemolysis solution |
| Wavelength (HbA1c-determine): | 658 nm (main)/805 nm (sub) |
| Measurement cycles: | 22/23-41/42 |

TABLE 2

| | Storage condition | | | | | | | | |
|---|---|---|---|---|---|---|---|---|---|
| | fresch | | | 11 d/2-8° C. | | | 7 d/37° C. + 4 d/2-8° C. | | |
| | TruCal HbA1c net | | | | | | | | |
| R2 | Level 1 | Level 2 | ΔmE | Level 1 | Level 2 | ΔmE | Level 1 | Level 2 | ΔmE |
| A) HbA1c calibration signals Consideration of various R2 varations with the same haemolysis solution (without $Zn^{2+}$) | | | | | | | | | |
| 6 mmol/L Ca | 6.9 | 11.3 | 4.5 | 6.8 | 11.8 | 5.0 | 6.8 | 10.1 | 3.4 |
| 12 μmol/L EDTA | 6.7 | 11.3 | | 7.0 | 11.9 | | 6.8 | 10.3 | |
| 6 mmol/L Ca | 6.6 | 11.1 | 4.5 | 6.8 | 11.3 | 4.7 | 6.8 | 10.5 | 3.4 |
| 1 mmol/L EDTA | 6.6 | 11.1 | | 6.7 | 11.5 | | 7.0 | 10.2 | |
| 0.5 mmol/L Ca | 6.5 | 11.1 | 4.7 | 6.5 | 11.1 | 4.6 | 6.3 | 10.3 | 4.0 |
| 12 μmol/L EDTA | 6.5 | 11.2 | | 6.5 | 11.1 | | 6.4 | 10.4 | |
| B) HbA1c calibration signals Consideration of various R2 varations with the same haemolysis solution (with $Zn^{2+}$) | | | | | | | | | |
| 6 mmol/L Ca | 16.7 | 32.9 | 16.1 | 17.1 | 34.1 | 16.9 | 13.4 | 25.8 | 12.5 |
| 12 μmol/L EDTA | 16.8 | 32.9 | | 17.0 | 33.8 | | 13.1 | 25.7 | |
| 6 mmol/L Ca | 29.8 | 70.2 | 40.1 | 29.2 | 69.8 | 41.1 | 19.2 | 52.5 | 32.8 |
| 1 mmol/L EDTA | 29.7 | 69.6 | | 29.0 | 70.5 | | 19.6 | 52.0 | |
| 0.5 mmol/L Ca | 30.1 | 71.2 | 41.6 | 21.2 | 46.8 | 25.7 | 12.4 | 26.4 | 14.1 |
| 12 μmol/L EDTA | 29.8 | 71.9 | | 20.8 | 46.7 | | 12.3 | 26.5 | |
| C) Consideration of signal loss over time compared to the respective fresh value | | | | | | | | | |
| 6 mmol/L Ca | | | | 0.5 | 1.3 | 0.8 | -3.2 | -7.0 | -3.7 |
| 12 μmol/L EDTA | | | | 0.2 | 0.9 | | -3.6 | -7.2 | |
| 6 mmol/L Ca | | | | -0.6 | -0.4 | 0.9 | -10.6 | -17.7 | -7.3 |
| 1 mmol/L EDTA | | | | -0.7 | 0.9 | | -10.1 | -17.6 | |
| 0.5 mmol/L Ca | | | | -8.9 | -24.4 | -15.9 | -17.8 | -44.8 | -27.5 |
| 12 μmol/L EDTA | | | | -9.0 | -25.2 | | -17.5 | -45.4 | |

It is to be deduced from Table 2 A) that no HbA1c determination is possible independently of the concentration of calcium ions and EDTA in the absence of zinc ions. The differing signal for Level 1 and Level 2 with different storage conditions is due to the different concentration of haemoglobin of the two calibrators.

Table 2 B) in contrast shows functionality of thermolysin in the presence of zinc ions with different ratios of calcium ions and EDTA. Table 2 C) shows the ΔmE loss of the individual calibrators under different storage conditions. Both batches with 6 mmol/L of calcium ions present a markedly smaller loss of signal in contrast to a batch with 0.5 mmol/L of calcium ions.

Specifically in regard to the storage condition for 7 days/37° C.+4 days/2-8° C. the difference between the two potassium concentrations with the same concentration of EDTA is significant. The results shown here impressively demonstrate the storage capability of an inactivated but structurally stabilised thermolysin in a liquid reagent matrix over various temperatures and time and the reactivatability thereof.

2. Stabilisation of the Unfolded Haemoglobin

Preceding efficient unfolding of haemoglobin and also stabilisation of that unfolded form are of essential significance for accurate measurement of Hb and HbA1c. For the purposes of stabilising the unfolded haemoglobin in haemolysis by a haemolytic detergent for example 2-(methacryloyloxyethyl)-2'-(trimethyl ammoniumethyl)phosphate polymer was added by way of example to the haemolysis solution base matrix in the following test and in that case a pH-value in the range of 1 to 3 was set.

These various haemolysis solution variations with and without additive were measured with respectively identical reagent 1 and reagent 2 on a clinical-chemical analyser Hitachi 912 (reagent compositions were used as specified in 1b) correspondingly modified as described in the Tables. To assess the stability of the haemolysate the haemolysate was produced manually (50 µL full blood sample+1000 µL per haemolysis solution (with and without additive of 2-(methacryloyloxyethyl)-2'-(trimethyl ammoniumethyl)phosphate polymer) and measured directly. The haemolysate was then stored open in the device at 15-25° C. and measured at various moments in time up to a maximum of 240 minutes after production of the haemolysates. In that case the signal of HbA1c determination was measured over a period of 240 minutes on the analyser and respectively related to the freshly ascertained HbA1c value. In that respect the following application formed the basis for measurement on the Hitachi 912:

| | |
|---|---|
| Reagent 1: | 240 µL |
| Reagent 3: | 80 µL |
| Haemolysated sample: | 40 µL |
| Wavelength (HbA1c-determine): | 660 nm (main)/800 nm (sub) |
| Measuring cycle: | 18-31 |

The results shown in FIG. 2a-d show a marked increase in stability for various sample materials with 2-(methacryloyloxyethyl)-2'-(trimethyl ammoniumethyl) phosphate polymer (with addition) in comparison with samples without 2-(methacryloyloxyethyl)-2'-(trimethyl ammoniumethyl) phosphate polymer (without addition), FIG. 2a-d. In detail the results of the following batches are shown in FIG. 2:

Figure a) TruCal HbA1c Level 1 without addition
Figure b) TruCal HbA1c Level 1 with addition
Figure c) low HbA1c, medium haemoglobin without addition
Figure d) low HbA1c, medium haemoglobin with addition By virtue of the illustrated results it has evidently been shown that the addition of 2-(methacryloyloxyethyl)-2'-(trimethyl ammoniumethyl)phosphate polymer to the haemolysis solution under the described conditions markedly improves stabilisation of the haemoglobin molecule, specified by 10% limits (broken line+/−10%) with respect to the respective freshly measured HbA1c determination.

3. Stabilisation of the Leuco Dye with Phosphines

To improve the stability of the leuco dye in a reagent matrix various water-soluble stable substances were checked in regard to their leuco dye-stabilising action. In that respect a reagent composition without stabiliser additive served as a negative reference and 1,3,5-triaza-7-phosphaadamantane served as the control substance as that substance does not correspond to the structural prerequisites.

The following reagent preparations by way of example were produced:

20 mM bis-tris buffer (bis(2-hydroyethyl)amino-tris(hydroxymethyl)methane)
20 mM Na-acetate
100 mM NaCl
6 mM Ca acetate
15 g/L Triton X 405
0.08 mM DA67 (leuco dye)
1000 U/ml thermolysin
1 mM EDTA Now a respective different stabilizer in respectively identical concentrations was added to the specified reagent base matrix without stabiliser. An aliquot without stabiliser substance served in that case as a reference.

The inherent absorption of the respective reagent composition was respectively measured (loading measurement) at 660 nm in each case directly after starting (fresh) and in each case after storage for 4 days at 37° C., using a photometer. The increase in 660 nm extinction in relation to time is in that case a measurement in respect of conversion of the leuco form of the dye into its coloured variant and thus a measurement in respect of oxidative destabilisation of the leuco form.

Under the above-specified conditions the results shown in Table 3 were achieved.

TABLE 3

Inherent colouring R2 at 660 nm in mE

| | Day 0 | Day 4 |
|---|---|---|
| Without stabiliser | 17.7 | 455 |
| TCEP | 15.7 | 37.9 |
| Bis(p-sulphonatophenyl)phenylphosphine dihydrate dipotassium salt | 19.2 | 164 |
| 1.3.5-Triaza-7-phosphaadamantane | 20.7 | 391 |
| Tris(3-sulphonatophenyl)phosphine hydrate sodium salt (<5% oxide) | 18.7 | 251 |
| Tris(hydroxymethyl)phosphine | 19.9 | 239 |
| Diphenyl(m-sulphonatophenyl)phosphine dihydrate sodium salt | 18.2 | 70 |
| [2-Dicyclohexylphosphino)ethyl]-trimethyl ammonium chlorid | 18.6 | 307 |

4. Stabilisation of the Leuco Dye with Thio Compounds

A plurality of thio compounds were checked in respect of their dye-stabilising action. For that purpose inherent colouring of a reagent solution (matrix of: NaCl, Ca acetate, Triton X 405+thermolysin, see in that respect composition 3), containing the leuco dye DA 67, was investigated after storage at 2-8° C. and 37° C. In that case the results shown in Table 4 were achieved for storage at 2-8° C.

TABLE 4

Inherent colouring R2 at 660 nm in mE

|  | Day 0 | Day 2 | Day 8 | Day 10 |
|---|---|---|---|---|
| Without additive | 50.1 | 136 | 344 | 463 |
| 0.1 mM TCEP | 20.4 | 23.4 | 48.1 | 106 |
| 0.2 mM TCEP | 14.2 | 18.7 | 41.6 | 97.4 |
| 2 mM thionicotinamide | 50.6 | 73.9 | 133.5 | 205 |
| 2 mM thionicotinamide + 0.2 mM TCEP | 9.6 | 17 | 41.5 | 91.8 |
| 4 mM thionicotinamide | 55.7 | 79.9 | 122 | 209 |
| 2 mM thio-NAD | 74.3 | 138 | 215 | 292 |
| 4 mM thio-NAD | 97.9 | 139 | 203 | 274 |
| 4 mM thionicotinamide + 0.1 mM TCEP | 26.7 | 36.3 | 55.5 | 106 |
| 2 mM thio-NAD + 0.2 mM TCEP | 11.1 | 34.6 | 56.6 | 105 |
| 4 mM thio-NAD + 0.1 mM TCEP | 21.3 | 46.3 | 68.3 | 128 |

The results shown in Table 5 were achieved for storage at 37° C.

TABLE 5

Inherent colouring R2 at 660 nm in mE

|  | Day 0 | Day 2 | Day 8 | Day 10 |
|---|---|---|---|---|
| Without additive | 50.1 | 610 | 2220 | 2513 |
| 0.1 mM TCEP | 20.4 | 23.4 | 66.2 | 646 |
| 0.2 mM TCEP | 14.2 | 18.7 | 31.9 | 295 |
| 2 mM thionicotinamide | 50.6 | 73.9 | 233 | 671 |
| 2 mM thionicotinamide + 0.2 mM TCEP | 9.6 | 17 | 41.5 | 29.7 |
| 4 mM thionicotinamide | 55.7 | 79.9 | 215 | 704 |
| 2 mM thio-NAD | 74.3 | 138 | 366 | 1174 |
| 4 mM thio-NAD | 97.9 | 139 | 305 | 893 |
| 4 mM thionicotinamide + 0.1 mM TCEP | 26.7 | 36.3 | 55.5 | 48.8 |
| 2 mM thio-NAD + 0.2 mM TCEP | 11.1 | 34.6 | 56.6 | 51.5 |
| 4 mM thio-NAD + 0.1 mM TCEP | 21.3 | 46.3 | 68.3 | 109 |

5. Stabilisation of the Leuco Dye with TCEP in Combination with Thio Compounds

A plurality of thio compounds were checked in respect of their dye-stabilising action upon use in combination with TCEP. For that purpose inherent colouring of a reagent solution (matrix of: buffer NaCl, Ca acetate, Triton X 405+thermolysin, see in that respect composition 3), containing the leuco dye DA 67, was investigated after storage at 2-8° C. and 37° C. In that case the results shown in Tables 6a and 6b were achieved for storage at 2-8° C.

TABLE 6a

Inherent colouring R2 at 660 nm in mE

|  | Day 0 | Day 2 | Day 8 | Day 10 |
|---|---|---|---|---|
| Without additive | 128 | 564 | 940 | 1124 |
| 2 mM S-NAD | 228 | 437 | 657 | 832 |
| 2 mM thionicotinamide | 73 | 189 | 268 | 319 |
| 2 mM NAD | 62 | 619 | 1248 | 1508 |
| 2 mM thiourea | 85 | 514 | 844 | 1056 |
| 1% 2.2 thiodiglycol | 96 | 211 | 299 | 357 |
| 0.1 mM TCEP | 89 | 111 | 129 | 266 |
| 2.2 thiodiglycol + TCEP 0.1 mM | 83 | 92 | 104 | 170 |

TABLE 6b

Inherent colouring R2 at 660 nm in mE

|  | Day 0 | Day 2 | Day 8 | Day 10 |
|---|---|---|---|---|
| Without additive | 115 | 323 | 848 | 1154 |
| 2 mM acetyl-NAD | 169 | 1097 | 1869 | 2037 |
| 2 mM thiomalic acid | 91 | 114 | 158 | 197 |

The results shown in Tables 7a and 7b were achieved for storage at 37° C.

TABLE 7a

Inherent colouring R2 at 660 nm in mE

|  | Day 0 | Day 2 | Day 8 | Day 10 |
|---|---|---|---|---|
| Without additive | 128 | 957 | 2583 | 2821 |
| 2 mM S-NAD | 228 | 437 | 662 | 1591 |
| 2 mM thionicotinamide | 73 | 189 | 292 | 862 |
| 2 mM NAD | 62 | 1220 | 2717 | 2940 |
| 2 mM thiourea | 85 | 514 | 594 | 2152 |
| 1% 2.2 thiodiglycol | 96 | 211 | 494 | 1730 |
| 0.1 mM TCEP | 89 | 111 | 219 | 1350 |
| 2.2 thiodiglycol + TCEP 0.1 mM | 83 | 92 | 104 | 272 |

TABLE 7b

Inherent colouring R2 at 660 nm in mE (separate batch)

|  | Day 0 | Day 2 | Day 8 | Day 10 |
|---|---|---|---|---|
| Without additive | 115 | 1183 | 2714 | 2885 |
| 2 mM acetyl-NAD | 169 | 1097 | 2024 | 3209 |
| 2 mM thiomalic acid | 91 | 114 | 188 | 341 |

6. Signal-Stabilising Effect of Thiodiglycol Alone or in Conjunction with TCEP

The HbA1c calibration signals were investigated in the presence of thioglycol alone or in conjunction with TCEP.

A reagent 2 base matrix (reagent compositions were used as specified in 1 b), correspondingly modified as described in the Tables), was mixed with 10 g/L β-thiodiglycol and parts of that base matrix mixed with respectively different concentrations of TCEP.

Those reagent 2 variations with respectively different haemolysis solution and reagent 1 were measured on a BM 6010c. For that purpose the DiaSys Calibrators TruCal HbA1c net (Article 1 3350) were used for that purpose. In that case the respective HbA1c determination was measured and assessed.

The application on which the measurement was based for the BM 6010c was in that case as follows:

| | |
|---|---|
| Reagent 1: | 90 μL |
| Reagent 3: | 30 μL |
| Haemolysated sample: | 15 μL |
| Haemolysis step: | 5 μL sample + 100 μL haemolysis solution |
| Wavelength (HbA1c-determine): | 6t58 nm (main)/805 nm (sub) |
| Measuring cycles: | 22/23-41/42 |

In that case the results shown in Table 8 were achieved.

TABLE 8

HbA1c calibration signals
Consideration of various TCRP concentrations with the same amount of β-thiodiglycol

| Reagent batch | fresh | | | 7 d/2-8° C. | | | 7 d/37° C. | | |
|---|---|---|---|---|---|---|---|---|---|
| | Level 1 | Level 2 | ΔmE | Level 1 | Level 2 | ΔmE | Level 1 | Level 2 | ΔmE |
| 10 g/L β-thiodiglycol without TCEP | 28.3 | 66.0 | 37.8 | 25.2 | 60.4 | 35.2 | 18.7 | 48.1 | 29.4 |
| 10 g/L β-thiodiglycol 0.1 mmol/L TCEP | 26.9 | 66.1 | 39.2 | 23.7 | 56.5 | 32.8 | 22.5 | 56.2 | 33.7 |
| 10 g/L β-thiodiglycol 0.2 mmol/L TCEP | 26.4 | 64.5 | 38.1 | 22.1 | 52.3 | 30.3 | 21.8 | 54.8 | 33.0 |
| 10 g/L βtThiodiglycol 0.3 mmol/L TCEP | 25.9 | 64.3 | 38.4 | 19.6 | 48.8 | 29.2 | 22.5 | 56.2 | 34.8 |
| 10 g/L β-thiodiglycol 0.4 mmol/L TCEP | 24.9 | 62.9 | 38.0 | 18.1 | 46.1 | 28.0 | 21.1 | 54.7 | 33.6 |
| 10 g/L β-thiodiglycol 0.5 mmol/L TCEP | 24.5 | 61.8 | 37.3 | 16.6 | 42.4 | 25.8 | 20.5 | 54.6 | 34.0 |

The signal drop in HbA1c determination at 7d/2-8° C. and at 7d/37° C. is evident when only thiodyglycol is used. The illustrated results in contrast clearly demonstrate the combinational use of TCEP and thiodiglycol at different TCEP concentrations.

The invention claimed is:
1. A method of determining the amount of glycated haemoglobin (HbA1c) in a sample, wherein the following method steps are performed:
   a) haemolysis of the erythrocytes in the sample to release the HbA1c contained therein,
   b) bringing the HbA1c released in method step a) into contact with a proteolytic agent for producing glycated haemoglobin degradation products, and
   c) determining the amount of HbA1c by quantification of the glycated haemoglobin degradation products produced in method step b),
   wherein the proteolytic agent used in method step b) is produced in that at least two different solutions are brought into contact with the HbA1c released in method step a), wherein the one solution has a pH value in the range of 1 to 8, and contains
   i) a metalloprotease,
   ii) per 1000 kU/l of metalloprotease 0.1 to 2 mmol/l of a chelator for divalent metal ions, and
   iii) 0.5 to 10 mmol/l $Ca^{2+}$ or 0.5 to 10 mmol/l $Mg^{2+}$, and wherein the molar ratio of chelator:$Ca^{2+}$ or chelator:$Mg^{2+}$ is in the range of 1:2 to 1:20 and the other solution contains 100 to 5000 μmol/l of a divalent metal ion selected from $Fe^{2+}$, $Mn^{2+}$, $Co^{2+}$ and $Zn^{2+}$.

2. The method according to claim 1, wherein the solution containing 100 to 5000 μmol/L of a divalent metal ion selected from $Fe^{2+}$, $Mn^{2+}$, $Co^{2+}$ and $Zn^{2+}$ is a haemolysis solution which is added in method step a) to the sample, that haemolysis solution containing a haemolytically acting detergent.

3. The method according to claim 1, wherein the haemolysis in method step a) is effected by adding a haemolysis solution (H), wherein the haemolysis solution has a haemolytically acting detergent and 2-(methacryloyloxyethyl)-2'-(trimethyl ammoniumethyl)phosphate polymer, a phosphatidylcholine or mixtures thereof and has a pH-value in the range of 1 to 3.

4. The method according to claim 1, wherein quantification of the glycated haemoglobin degradation products in method step c) is effected by oxidation thereof by means of fructosyl peptide oxidase or fructosyl amino acid oxidase with production of hydrogen peroxide and by determining the resulting amount of hydrogen peroxide, wherein the amount of hydrogen peroxide is quantified by means of the colour reaction of a leuco dye in the presence of a peroxidase, and wherein the leuco dye is prepared in a solution which for stabilisation of the dye contains a compound represented by formula (I):

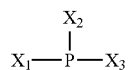

wherein P stands for a phosphorus atom and wherein $X_1$, $X_2$ and $X_3$ are selected independently of each other from the group consisting of straight-chain or branched-chain $C_1C_8$-alkyl residues, cyclohexyl residues and phenyl residues.

5. The method according to claim 4, wherein the compound is selected from the group consisting of: tris(2-carboxyethyl)phosphatin (TCEP), bis(p-sulphonatophenyl)phenylphosphine dihydrate dipotassium salt, 1,3,5-triaza-7-phosphine adamantane, tris(3-sulphonatophenyl)phosphine hydrate sodium salt, tris(4,6-dimethyl-3-sulphonatophenyl)phosphine trisodium salt hydrate, tris(hydroxymethyl)phosphine, di-t-butyl(3-sulphonatopropyl)phosphine, diphenyl(m-sulphonatophenyl)phosphine dehydrate sodium salt, and [2-dicyclohexylphosphino)ethyl]-trimethyl ammonium chloride.

6. The method according to claim 4, wherein the solution containing the leuco dye for stabilisation of the dye contains at least one thio compound.

7. The method according to claim 6, wherein the at least one thio compound is selected from thiodiglycol, thiomalic acid, thionicotinamide, thio-NAD and mixtures thereof.

8. The method according to claim 6, wherein prior to carrying out the operation of determining the amount of HbA1c in method step c) an SH group-trapping agent is added to the reaction mixture.

9. The method according to claim 1, wherein an operation for determining the total haemoglobin concentration is carried out during or between method steps a)-c).

10. A reagent kit for use in a method of determining the amount of glycated haemoglobin (HbA1c) in a sample, wherein the reagent kit includes at least two different solutions in separate containers, wherein the one solution has a pH-value in the range of 1 to 8 and contains a metalloprotease and per 1000 kU/l of metalloprotease 0.1 to 2 mmol/l of a chelator for divalent metal ions and 0.5 to 10 mmol/l $Ca^{2+}$ or 0.5 to 10 mmol/l $Mg^{2+}$, wherein the molar ratio of chelator:$Ca^{2+}$ or chelator:$Mg^{2+}$ is in the range of 1:2 to 1:20 and the other solution contains 100 to 5000 µmol/l of a divalent metal ion selected from $Fe^{2+}$, $Mn^{2+}$, $Co^{2+}$ and $Zn^{2+}$.

11. The reagent kit according to claim 10, wherein the solution (H) is a haemolysis solution which contains a haemolytically acting detergent and in addition 2-(methacryloyloxyethyl)-2'-(trimethyl ammoniumethyl)phosphate polymer, a phosphatidylcholine or mixtures there-of and has a pH-value in the range of 1 to 3.

12. The reagent kit according to claim 10, wherein it includes at least the following solutions in separate containers:

a haemolysis solution (H) containing a haemolytically acting detergent and 100 to 5000 µmol/L of a divalent metal ion selected from $Fe^{2+}$, $Mn^{2+}$, $Co^{2+}$ and $Zn^{2+}$, a first reagent solution (R1) containing fructosyl peptide oxidase or fructosyl amino acid oxidase and peroxidase, and a second reagent solution (R2) additionally containing a metalloprotease and per 1000 kU/l of metalloprotease 0.1 to 2 mmol/l of a chelator for divalent metal ions and 0.5 to 10 mmol/l of $Ca^{2+}$ or 0.5 to 10 mmol/l of $Mg^{2+}$, wherein the molar ratio of chelator:$Ca^{2+}$ and chelator:$Mg^{2+}$ is in the range of 1:2 to 1:20, and a leuco dye.

13. The reagent kit according to claim 12, wherein the solution (R2) for stabilisation of the dye contains at least one compound represented by formula (I):

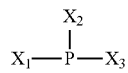

wherein P stands for a phosphorus atom and wherein $X_1$, $X_2$ and $X_3$ are selected independently of each other from the group consisting of straight-chain or branched-chain $C_1C_8$-alkyl residues, cyclohexyl residues and phenyl residues.

14. The reagent kit according to claim 13, wherein the compound is selected from the group consisting of: tris(2-carboxyethyl)phosphatin (TCEP), bis(p-sulphonatophenyl)phenylphosphine dihydrate dipotassium salt, 1,3,5-triaza-7-phosphine adamantane, tris(3-sulphonatophenyl)phosphine hydrate sodium salt, tris(4,6-dimethyl-3-sulphonatophenyl)phosphine trisodium salt hydrate, tris(hydroxymethyl)phosphine, di-t-butyl(3-sulphonatopropyl)phosphine, diphenyl(m-sulphonatophenyl)phosphine dehydrate sodium salt, and [2-dicyclohexylphosphino)ethyl]-trimethyl ammonium chloride.

15. The reagent kit according to claim 12, wherein the solution (R2) for stabilising the leuco dye contains at least one thio compound.

16. The reagent kit according to claim 15, wherein the at least one thioalcohol is selected from the group consisting of thiodiglycol, thiomalic acid, thionicotinamide, thio-NAD, and mixtures thereof.

17. The reagent kit according to claim 12, wherein the solution (R1) contains an SH group-trapping agent.

18. The reagent kit according to claim 17, wherein the SM group-trapping agent is N-ethylmaleinimide.

* * * * *